(12) United States Patent
Lu

(10) Patent No.: US 11,433,906 B2
(45) Date of Patent: Sep. 6, 2022

(54) VEHICULAR DRIVER MONITORING SYSTEM WITH HEART RATE MEASUREMENT

(71) Applicant: Magna Electronics Inc., Auburn Hills, MI (US)

(72) Inventor: Yuesheng Lu, Farmington Hills, MI (US)

(73) Assignee: MAGNA ELECTRONICS INC., Auburn Hills, MI (US)

( * ) Notice: Subject to any disclaimer, the term of this patent is extended or adjusted under 35 U.S.C. 154(b) by 0 days.

(21) Appl. No.: 16/946,848

(22) Filed: Jul. 9, 2020

(65) Prior Publication Data

US 2021/0009141 A1    Jan. 14, 2021

Related U.S. Application Data

(60) Provisional application No. 62/872,779, filed on Jul. 11, 2019.

(51) Int. Cl.
| | |
|---|---|
| *H04N 5/44* | (2011.01) |
| *B60W 40/08* | (2012.01) |
| *B60W 50/14* | (2020.01) |
| *B60R 1/00* | (2022.01) |
| *G06T 7/73* | (2017.01) |
| *G06V 20/59* | (2022.01) |
| *G06V 40/16* | (2022.01) |

(52) U.S. Cl.
CPC ............... *B60W 40/08* (2013.01); *B60R 1/00* (2013.01); *B60W 50/14* (2013.01); *G06T 7/74* (2017.01); *G06V 20/597* (2022.01); *G06V 40/162* (2022.01); *B60R 2300/103* (2013.01); *B60R 2300/8006* (2013.01); *B60W 2040/0872* (2013.01); *B60W 2540/221* (2020.02); *B60W 2540/229* (2020.02); *G06T 2207/30201* (2013.01)

(58) Field of Classification Search
CPC ................ B60W 40/08; B60W 50/14; B60W 2040/0872; B60W 2540/221; B60W 2540/229; B60R 1/00; B60R 2300/103; B60R 2300/8006; G06T 7/74; G06T 2207/30201; G06V 20/597; G06V 40/162
See application file for complete search history.

(56) References Cited

U.S. PATENT DOCUMENTS

| | | | |
|---|---|---|---|
| 5,550,677 | A | 8/1996 | Schofield et al. |
| 5,670,935 | A | 9/1997 | Schofield et al. |
| 5,949,331 | A | 9/1999 | Schofield et al. |
| 6,485,081 | B1 | 11/2002 | Bingle et al. |
| 6,621,411 | B2 | 9/2003 | McCarthy et al. |
| 6,762,676 | B2 | 7/2004 | Teowee et al. |

(Continued)

*Primary Examiner* — Munear T Akki
(74) *Attorney, Agent, or Firm* — Honigman LLP

(57) ABSTRACT

A driver monitoring system for a vehicle includes a camera and an ECU. The camera is disposed at an interior of the vehicle so as to view the face of a driver of the vehicle. The camera captures image data and the captured image data includes image data representative of the face of the driver. The ECU includes electronic circuitry and associated software, with the electronic circuitry including an image processor that processes image data captured by the camera. The ECU, responsive to processing by the image processor of image data captured by the camera, determines a heart rate of the driver.

13 Claims, 7 Drawing Sheets

(56) References Cited

U.S. PATENT DOCUMENTS

| | | | | |
|---|---|---|---|---|
| 8,063,786 B2* | 11/2011 | Manotas, Jr. | ........ | G08B 21/06 340/576 |
| 8,258,932 B2 | 9/2012 | Wahlstrom | | |
| 9,750,420 B1* | 9/2017 | Agrawal | ........ | G06T 7/73 |
| 9,988,055 B1* | 6/2018 | O'Flaherty | ........ | G08B 21/02 |
| 2007/0055164 A1* | 3/2007 | Huang | ........ | A61B 5/6887 340/576 |
| 2007/0257804 A1* | 11/2007 | Gunderson | ........ | G07C 5/0891 340/576 |
| 2009/0156904 A1* | 6/2009 | Shen | ........ | A61B 5/6888 600/300 |
| 2012/0150387 A1* | 6/2012 | Watson | ........ | A61B 5/0077 701/1 |
| 2014/0167967 A1* | 6/2014 | He | ........ | B60W 50/16 340/576 |
| 2014/0306814 A1* | 10/2014 | Ricci | ........ | G08G 1/01 340/425.5 |
| 2014/0336876 A1 | 11/2014 | Gieseke et al. | | |
| 2015/0009010 A1 | 1/2015 | Biemer | | |
| 2015/0015710 A1 | 1/2015 | Tiryaki | | |
| 2015/0022664 A1 | 1/2015 | Pflug et al. | | |
| 2015/0232030 A1 | 8/2015 | Bongwald | | |
| 2015/0258892 A1* | 9/2015 | Wu | ........ | G06V 40/166 340/576 |
| 2015/0294169 A1 | 10/2015 | Zhou et al. | | |
| 2015/0296135 A1 | 10/2015 | Wacquant et al. | | |
| 2015/0352953 A1 | 12/2015 | Koravadi | | |
| 2016/0090097 A1* | 3/2016 | Grube | ........ | G08B 21/06 340/576 |
| 2016/0137126 A1 | 5/2016 | Fursich et al. | | |
| 2017/0274906 A1 | 9/2017 | Hassan et al. | | |
| 2017/0367590 A1* | 12/2017 | Sebe | ........ | G06V 40/176 |
| 2020/0143560 A1 | 5/2020 | Lu et al. | | |
| 2020/0163560 A1* | 5/2020 | Chang | ........ | G06V 40/171 |
| 2020/0214614 A1* | 7/2020 | Rundo | ........ | G06N 3/0445 |
| 2020/0283001 A1 | 9/2020 | Kulkarni | | |

\* cited by examiner

VEHICULAR DRIVER MONITORING SYSTEM WITH HEART RATE MEASUREMENT

CROSS REFERENCE TO RELATED APPLICATION

The present application claims priority of U.S. provisional application Ser. No. 62/872,779, filed Jul. 11, 2019, which is hereby incorporated herein by reference in its entirety.

FIELD OF THE INVENTION

The present invention relates generally to a vehicle vision system for a vehicle and, more particularly, to a vehicle vision system that utilizes one or more cameras at an interior cabin of the vehicle.

BACKGROUND OF THE INVENTION

Use of imaging sensors in vehicle imaging systems is common and known. Examples of such known systems are described in U.S. Pat. Nos. 5,949,331; 5,670,935 and/or 5,550,677, which are hereby incorporated herein by reference in their entireties.

SUMMARY OF THE INVENTION

The present invention provides a driver monitoring system that utilizes one or more cameras to capture image data representative of images interior of the vehicle, and that provides heart rate measurement and/or other vital signs via processing of image data captured by the camera(s). A control includes an image processor operable to process image data captured by the camera. The control, responsive to image processing of image data captured by the camera, monitors the imaged portion of the driver (such as a region of the driver's face) and determines the driver's heart rate and other physical characteristics that pertain to the health and/or status of the driver. The driver monitoring system may also monitor the eyes and/or head of the driver to determine attentiveness or drowsiness of the driver. Responsive to determination of a threshold change in heart rate and/or attentiveness below a threshold level, the system may generate an alert and/or may generate an output to cause a vehicle control system to take over control or partial control of the vehicle.

These and other objects, advantages, purposes and features of the present invention will become apparent upon review of the following specification in conjunction with the drawings.

DESCRIPTION OF THE PREFERRED EMBODIMENTS

A vehicle vision system and/or driver assist system and/or object detection system and/or alert system operates to capture images exterior and/or interior of the vehicle and may process the captured image data to monitor occupants of the vehicle and/or display images and to detect objects at or near the vehicle and in the predicted path of the vehicle, such as to assist a driver of the vehicle in maneuvering the vehicle in a rearward direction. The vision system includes an image processor or image processing system that is operable to receive image data from one or more cameras and provide an output to a display device for displaying images representative of the captured image data.

Figure 1:
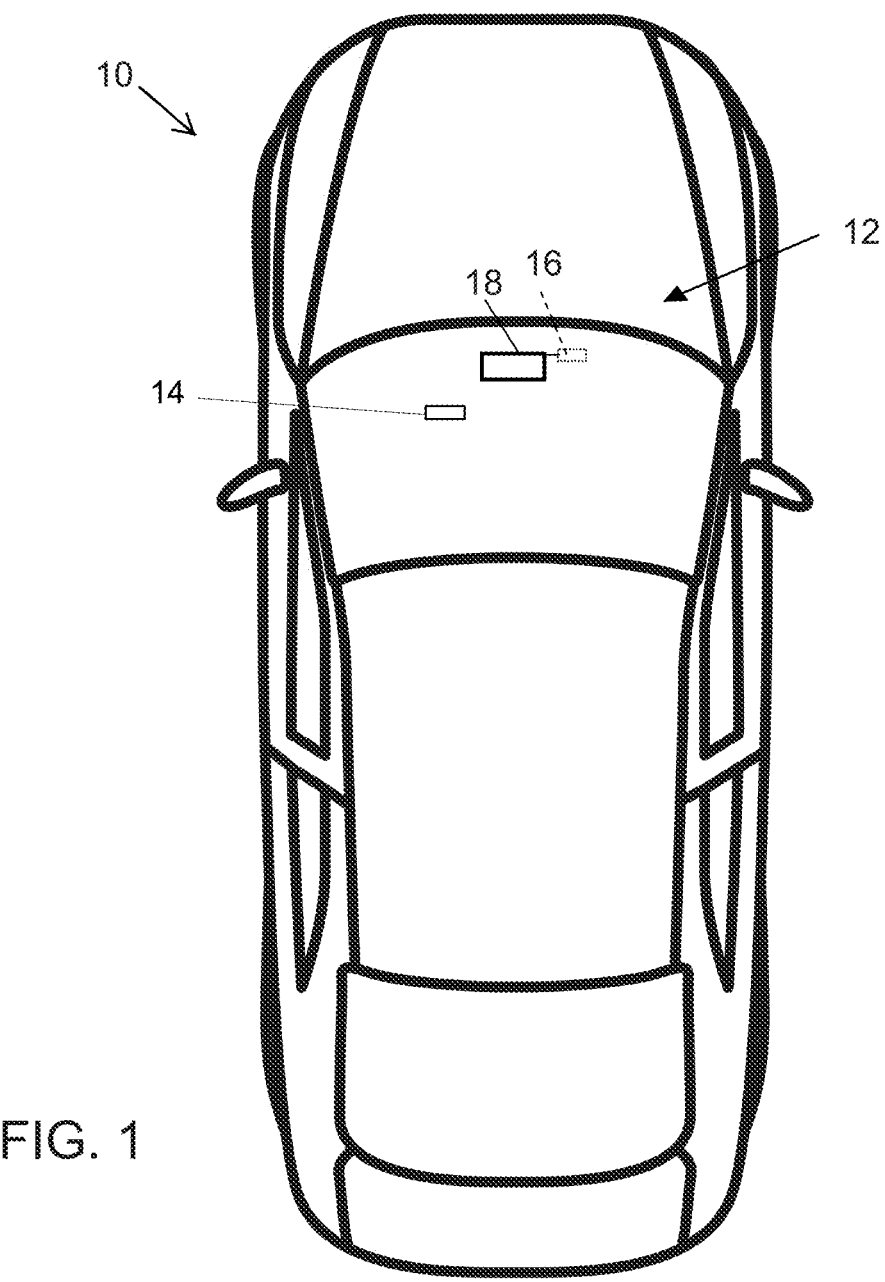
FIG. 1 is a plan view of a vehicle with a driver monitoring system that incorporates cameras in accordance with the present invention.

Referring now to the drawings and the illustrative embodiments depicted therein, a vehicle 10 includes a driver monitoring system 12 that includes at least one interior viewing imaging sensor or camera 14, with the camera having a lens for focusing images at or onto an imaging array or imaging plane or imager of the camera (FIG. 1). The system 12 includes a control or electronic control unit (ECU) 16 that comprises electronic circuitry and associated software, with the electronic circuitry including a data processor or image processor that is operable to process image data captured by the camera or cameras (and may process image data captured by other cameras at the vehicle, such as exterior viewing cameras disposed at locations so as to have respective fields of view exterior of the vehicle) and/or may provide an output to a display device 18 for displaying video images for viewing by the driver of the vehicle. The data transfer or signal communication from the camera to the ECU may comprise any suitable data or communication link, such as a vehicle network bus or the like of the equipped vehicle.

The driver monitoring system includes a driver monitoring camera 14 that captures image data representative of the driver's head. The camera is disposed at a dashboard or instrument panel of the vehicle and has the principal axis of its field of view directed toward the face of the driver.

The driver monitoring system may track the head and eyes of the driver of the vehicle. To accurately track the eyes of the driver, the pupils of the eyes must be clearly viewed by a camera or other imaging device. Because of this, a preferred camera position is directly in front of the driver and at or below a line-of-sight to the road. This allows the camera to view both pupils in most situations and also avoid having the driver's eyelashes in the way (which is a problem that occurs when cameras are mounted above the line-of-sight to the road).

Figure 2:
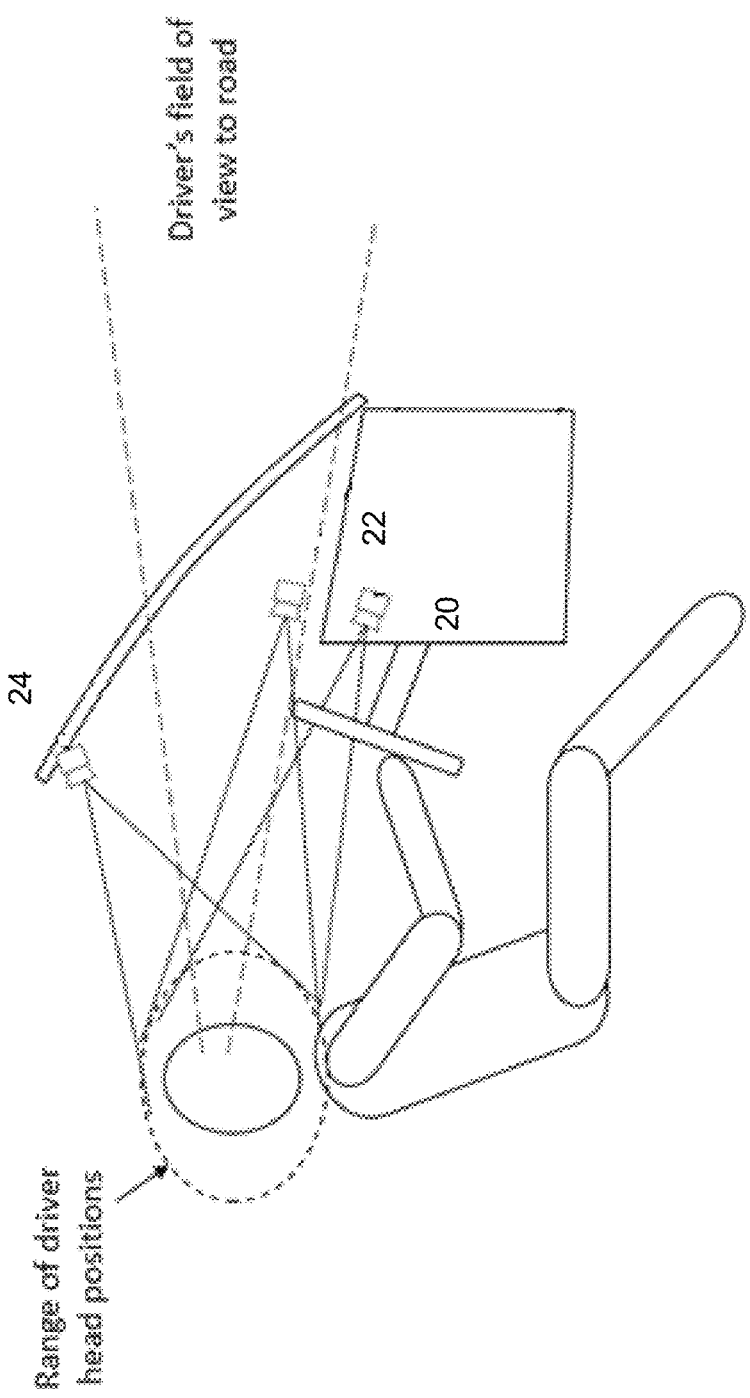
FIG. 2 is a side view of optional locations for cameras in the driver monitoring system.
Figure 3:
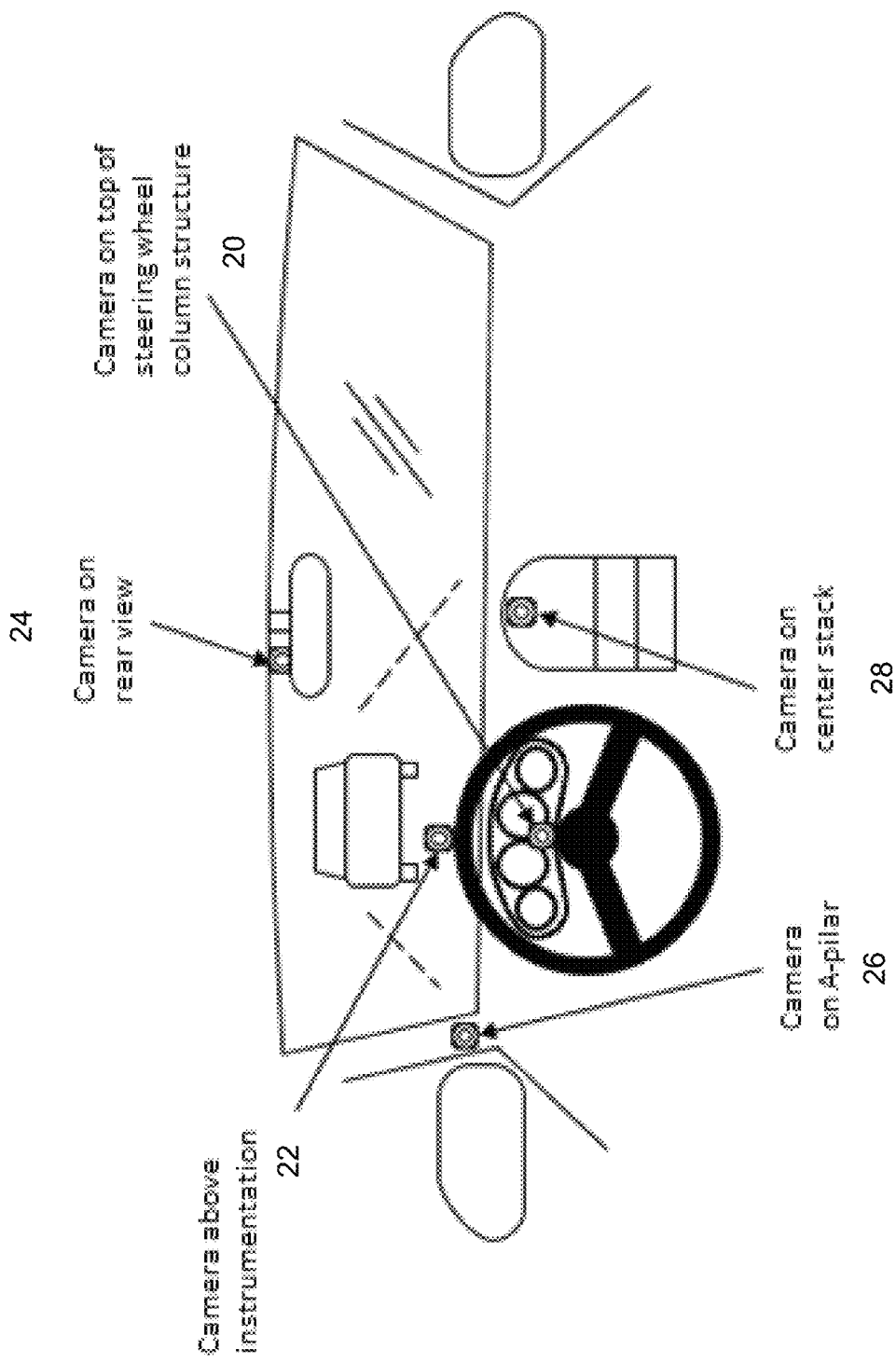
FIG. 3 is a forward view from inside the vehicle cabin of optional locations for cameras in the driver monitoring system.
Figure 4:
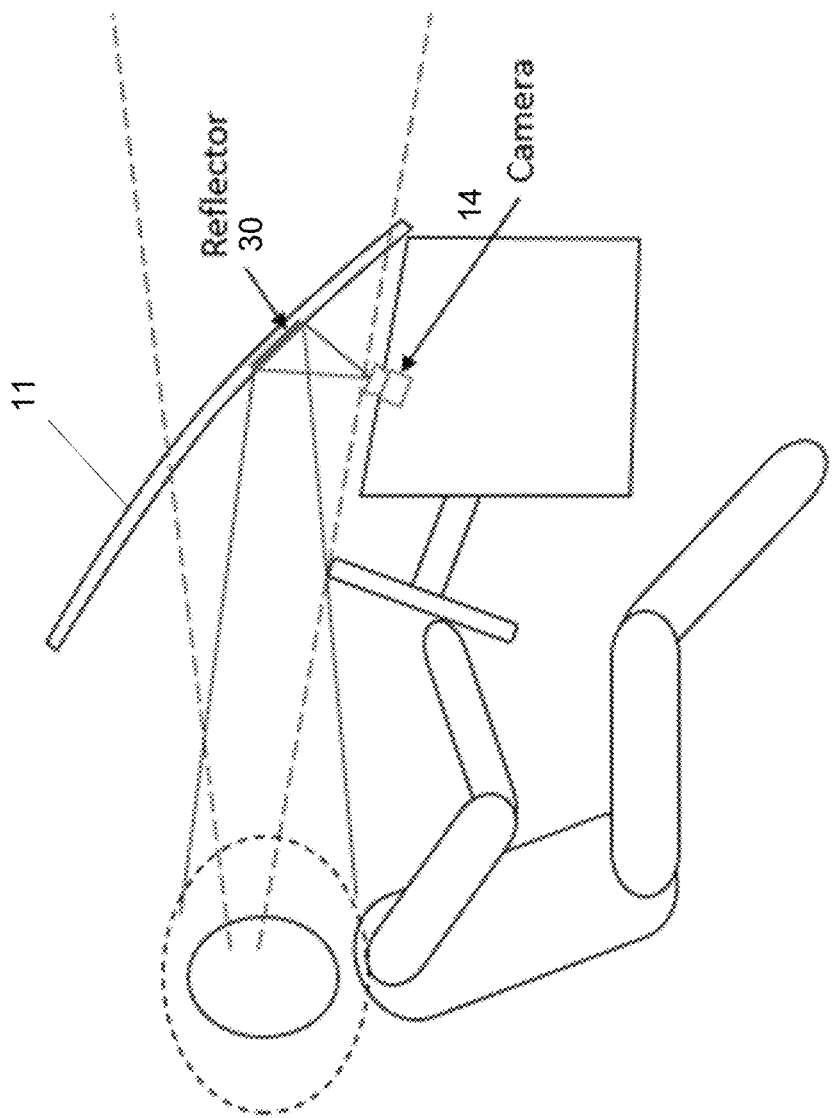
FIG. 4 is a side view of another location for a camera and reflector in the driver monitoring system.
Figure 5:
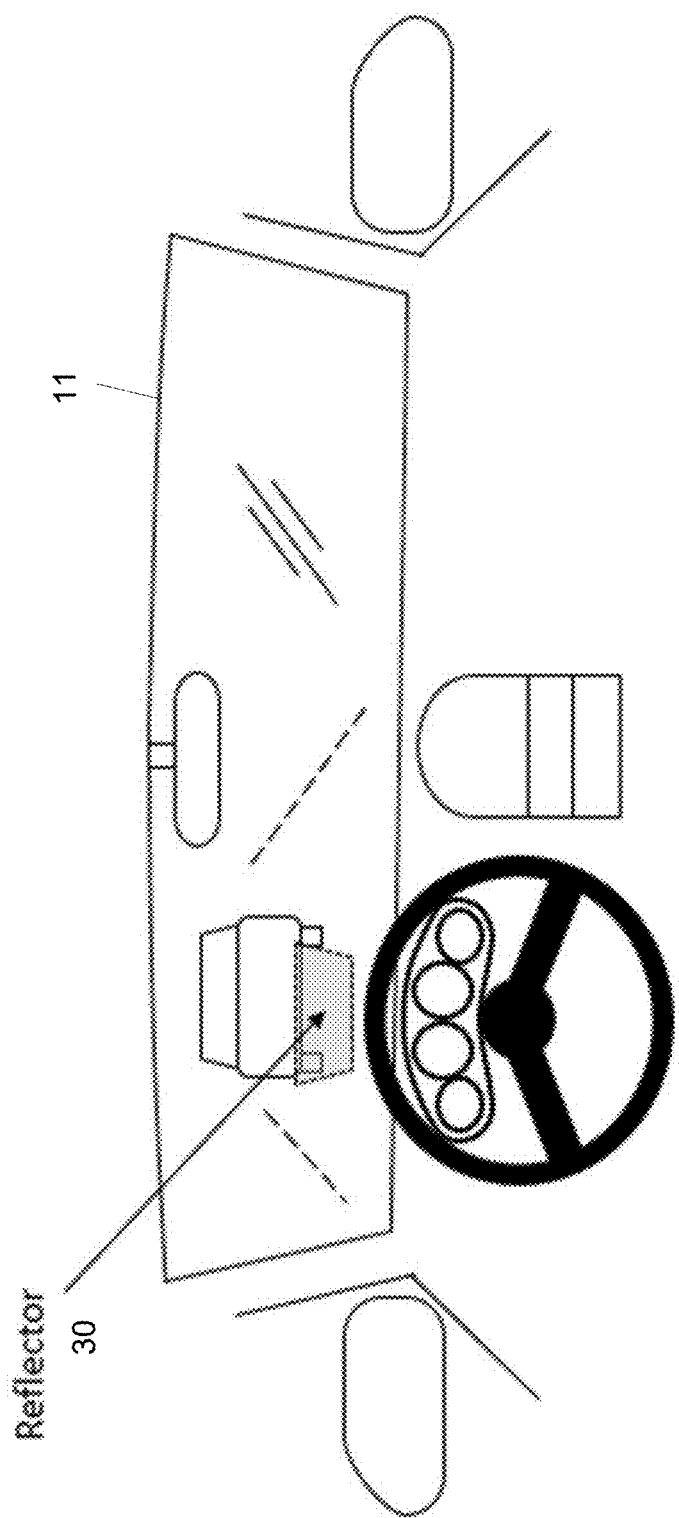
FIG. 5 is forward view from inside the vehicle cabin of the camera and reflector and driver monitoring system of FIG. 4.

As shown in FIGS. 2 and 3, one location for mounting the camera or cameras in a driver monitoring system is at a position 20 near the instrument cluster where the camera views the driver through the steering wheel opening. The camera is either placed on the steering column or in the dashboard somewhere near or within the instrument cluster. A camera may also or otherwise be mounted in a position 22 directly above the steering wheel, or at a position 24 at the interior rearview mirror assembly (which may also incorporate a video display and/or the control unit or the like), or at either or both of positions 26 (at the A-pillar) or 28 (at the center stack or instrument panel), such as shown in FIG. 3. Optionally, and such as shown in FIGS. 4 and 5, a camera 14 may be directed toward a portion of the windshield 11 of the vehicle where a reflector 30 is disposed, such as by utilizing aspects of the systems described in U.S. Publication No. US-2020-0143560, which is hereby incorporated herein by reference in its entirety. The reflector comprises a thin film or coating disposed at the windshield portion that reflects infrared (IR) or near-infrared (NIR) light and allows visible light to pass therethrough. The IR/NIR light present at the driver's head region is imaged by the camera 14 for the driver monitoring system via reflection of the IR/NIR light off the reflector 30.

The driver (and/or passenger) monitoring system (comprising the camera(s) and a controller or control unit having a processor for processing image data captured by the camera(s)) can also operate as a remote Photoplethysmography (rPPG) system to monitor human's heart rate, and optionally other vital signs. The system, responsive to detection of a change of the driver's heartbeat, may determine if the driver's capability of driving the vehicle is impaired, such as due to the driver having a health issue, the driver being tired or drowsy, the driver being stressed, or the driver being drunk or under drug influence of the like. The system may generate an alert or warning (such as to the driver or to a passenger in the vehicle or to a remote system or control remote from the vehicle) if the system determines a health issue or the like with the driver.

Figure 6:
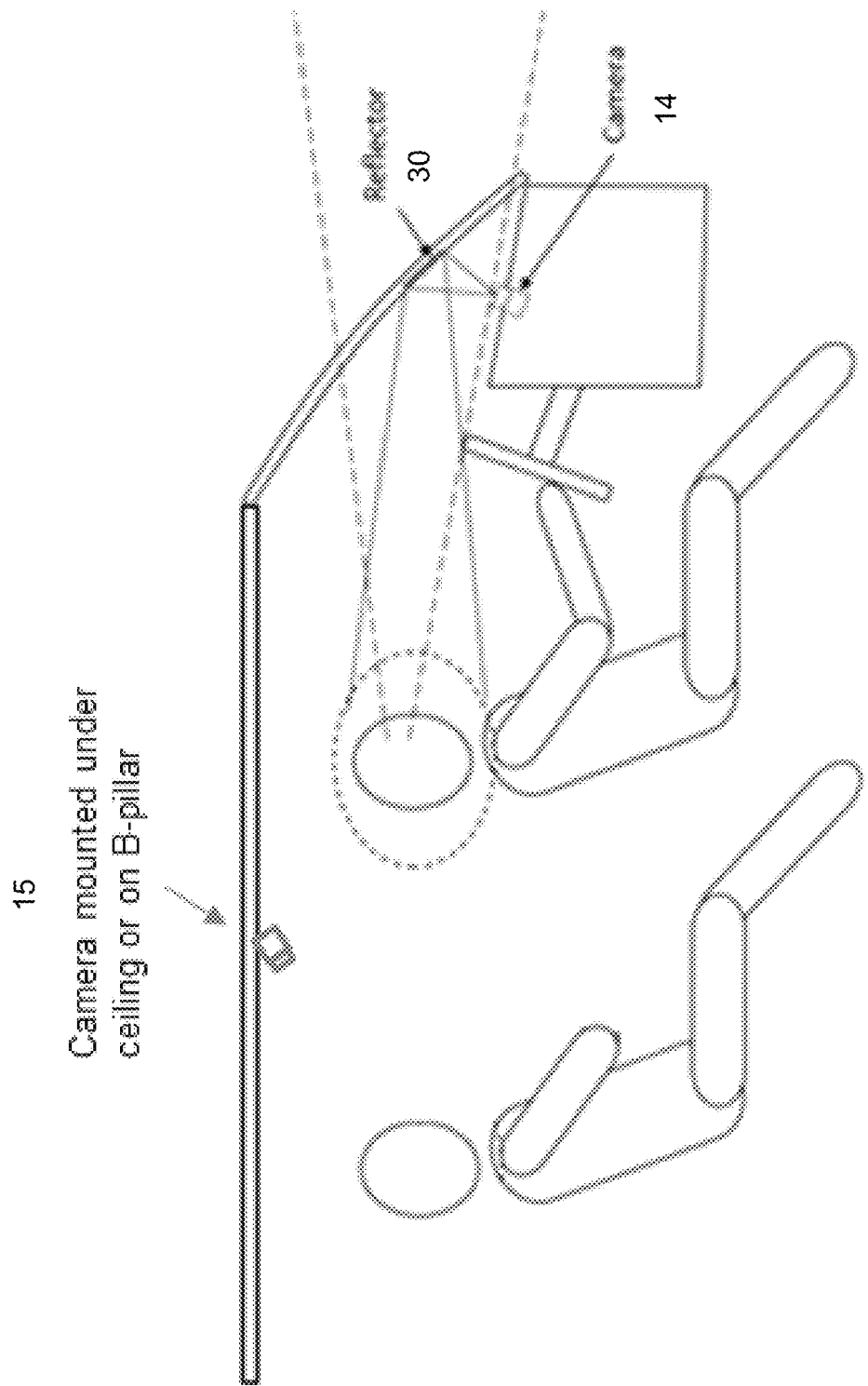
FIG. 6 is a side view of the driver monitoring system of FIG. 4, showing another camera mounted at the ceiling or B-pillar for a rear seat passenger monitoring system.

Optionally, and such as shown in FIG. 6, the system may include another camera 15 that monitors or views occupants of one or more passenger seats (such as rear seats or such as the front passenger seat) and may determine if the passenger has a health issue that needs attention. If such a determination is made, the system generates an alert or warning, such as to the driver or to the passenger or another passenger in the vehicle or to a remote system or control remote from the vehicle.

Because blood flows into vessels in the human head, the blood flow can cause facial skin to change optical reflection at a certain color spectrum, or can cause the head to move in a tiny degree, that are normally not detectable by human eyes. The optical reflection or head movement is in synchronization with the person's heartbeat.

Figure 7:
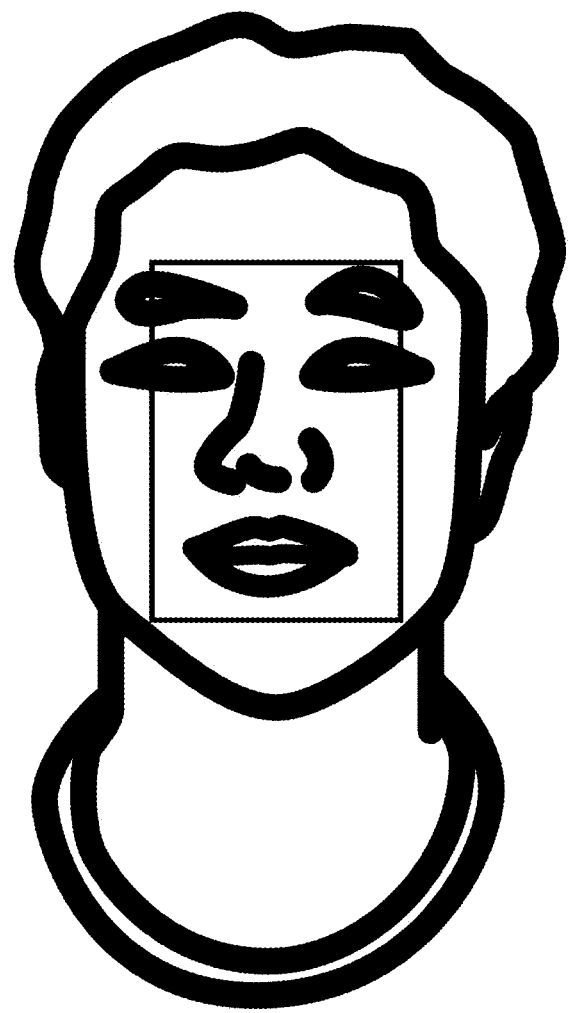
FIG. 7 is a view of a person's face, showing a region of interest where the monitoring system detects changes in color, reflection, movement to determine the person's heartbeat.

The interior camera(s) can be used to capture image data representative of the driver or passenger head and face, and computational algorithms are used to detect the tiny skin color changes and/or tiny head movements. For example, a camera imaging the driver/passenger head can be used to transmit video or captured image data to an image processing unit that runs special algorithms that extract heartbeat frequency from the video image data. Optionally, one region of interest (ROI) or multiple regions of interest on driver/passenger's face (such as a region that includes or encompasses the driver's eyes, nose and mouth, such as the rectangular region shown in FIG. 7) are used to determine or measure facial optical reflection and/or head movement and to extract changes in facial reflection, whereby the system processes the captured image data to extract or determine the heartrate signal.

Natural light can be used as the illumination and a normal visible spectrum camera can used. The camera may comprise a CMOS image sensor (comprising one million or more photosensing elements arranged in a two dimensional array of rows and columns) with a red-green-green-blue or RGGB (Bayer), red-clear-clear-blue or RCCB, red-clear-clear-clear or RCCC, red-green-blue-IR or RGB-IR or other color or spectral filter array pattern at the image sensor array.

Optionally, an infrared or near-infrared light emitting diode (LED) or other light source may be disposed in the vehicle that directs IR/NIR light toward the driver's head region, whereby the camera images the illuminated driver's head. The LED and camera may operate together when the driver monitoring system is operating. The LED may be disposed at the camera or integrated with the camera or the LED may be disposed elsewhere in the vehicle (such as close to the camera) so as to emit light generally directly toward the driver's head region.

Because the infrared (IR) or near IR (NIR) spectrum is more sensitive to human blood than other optical spectrums, such an IR or NIR light emitting diode (LED) or laser is preferably used as an illuminator to enhance the camera's image sensitivity and to decrease/eliminate the environment light's uncontrolled illumination, thereby increasing measurement accuracy of the system. Synchronization of the illumination source's pulse with the imager's exposure further increases the vision signal and decreases noise from environmental lights and electrical circuits. Optionally, for example, an imager with a global shutter (e.g., and On Semi AR0234 or AR0144 imager) may be used to better synchronize image exposure with pulsed illuminations.

Therefore, the present invention provides a driver monitoring system or passenger monitoring system that processes image data captured by a camera (such as a camera having a high definition multi-megapixel color CMOS imager) to determine the driver's or passenger's heartbeat. This is accomplished via detecting small changes in color of the person's skin and/or small movements of the person's head as blood flows into vessels in the person's head. By detecting such small (not perceivable to the human eye) color changes and/or head movements (indicative of blood flow), the system can determine the heartbeat or heart rate of the person and can determine changes in the heartbeat that may be indicative of a health issue. If such changes (such as a rapid increase or decrease in heart rate that is greater than a threshold change over a predetermined period of time, or such as an increase in heart rate above a threshold or normal level, or such as a slowing of the heart beat below a threshold or normal level) are detected, the system may generate an alert to the driver or passenger or to a remote server or device located remotely from the vehicle. For example, the system may generate an alert to the emergency contact for the driver or may generate an alert to a medical facility or service, depending on the severity of the detected changes. Optionally, the system may generate an output that causes an autonomous control system to take over driving of the vehicle, whereby the vehicle may be controlled to stop at the side of the road as soon as possible or to drive to the nearest medical facility.

The driver monitoring system may utilize aspects of head and face direction and position tracking systems and/or eye tracking systems and/or gesture recognition systems. Such head and face direction and/or position tracking systems and/or eye tracking systems and/or gesture recognition systems may utilize aspects of the systems described in U.S. Publication Nos. US-2017-0274906; US-2016-0137126; US-2015-0352953; US-2015-0296135; US-2015-0294169; US-2015-0232030; US-2015-0022664; US-2015-0015710; US-2015-0009010 and/or US-2014-0336876, which are hereby incorporated herein by reference in their entireties.

The camera or sensor may comprise any suitable camera or sensor. Optionally, the camera may comprise a "smart camera" that includes the imaging sensor array and associated circuitry and image processing circuitry and electrical connectors and the like as part of a camera module, such as by utilizing aspects of the vision systems described in International Publication Nos. WO 2013/081984 and/or WO 2013/081985, which are hereby incorporated herein by reference in their entireties.

For example, the vision system and/or processing and/or camera and/or circuitry may utilize aspects described in U.S. Pat. Nos. 9,233,641; 9,146,898; 9,174,574; 9,090,234; 9,077,098; 8,818,042; 8,886,401; 9,077,962; 9,068,390; 9,140,789; 9,092,986; 9,205,776; 8,917,169; 8,694,224; 7,005,974; 5,760,962; 5,877,897; 5,796,094; 5,949,331; 6,222,447; 6,302,545; 6,396,397; 6,498,620; 6,523,964; 6,611,202; 6,201,642; 6,690,268; 6,717,610; 6,757,109; 6,802,617; 6,806,452; 6,822,563; 6,891,563; 6,946,978; 7,859,565; 5,550,677; 5,670,935; 6,636,258; 7,145,519; 7,161,616; 7,230,640; 7,248,283; 7,295,229; 7,301,466; 7,592,928; 7,881,496; 7,720,580; 7,038,577; 6,882,287; 5,929,786 and/or 5,786,772, and/or U.S. Publication Nos. US-2014-0340510; US-2014-0313339; US-2014-0347486; US-2014-0320658; US-2014-0336876; US-2014-0307095; US-2014-0327774; US-2014-0327772; US-2014-0320636; US-2014-0293057; US-2014-0309884; US-2014-0226012; US-2014-0293042; US-2014-0218535; US-2014-0218535; US-2014-0247354; US-2014-0247355; US-2014-0247352; US-2014-0232869; US-2014-0211009; US-2014-0160276; US-2014-0168437; US-2014-0168415; US-2014-0160291; US-2014-0152825; US-2014-0139676; US-2014-0138140; US-2014-0104426; US-2014-0098229; US-2014-0085472; US-2014-0067206; US-2014-0049646; US-2014-0052340; US-2014-0025240; US-2014-0028852; US-2014-005907; US-2013-0314503; US-2013-0298866; US-2013-0222593; US-2013-0300869; US-2013-0278769; US-2013-0258077; US-2013-0258077; US-2013-0242099; US-2013-0215271; US-2013-0141578 and/or US-2013-0002873, which are all hereby incorporated herein by reference in their entireties. The system may communicate with other communication systems via any suitable means, such as by utilizing aspects of the systems described in International Publication Nos. WO 2010/144900; WO 2013/043661 and/or WO 2013/081985, and/or U.S. Pat. No. 9,126,525, which are hereby incorporated herein by reference in their entireties.

The imaging device and control and image processor and any associated illumination source, if applicable, may comprise any suitable components, and may utilize aspects of the cameras (such as various imaging sensors or imaging array sensors or cameras or the like, such as a CMOS imaging array sensor, a CCD sensor or other sensors or the like) and vision systems described in U.S. Pat. Nos. 5,760,962; 5,715,093; 6,922,292; 6,757,109; 6,717,610; 6,590,719; 6,201,642; 5,796,094; 6,559,435; 6,831,261; 6,822,563; 6,946,978; 7,720,580; 8,542,451; 7,965,336; 7,480,149; 5,877,897; 6,498,620; 5,670,935; 5,796,094; 6,396,397; 6,806,452; 6,690,268; 7,005,974; 7,937,667; 7,123,168; 7,004,606; 6,946,978; 7,038,577; 6,353,392; 6,320,176; 6,313,454 and/or 6,824,281, and/or International Publication Nos. WO 2009/036176; WO 2009/046268; WO 2010/099416; WO 2011/028686 and/or WO 2013/016409, and/or U.S. Publication Nos. US 2010-0020170 and/or US-2009-0244361, which are all hereby incorporated herein by reference in their entireties.

Changes and modifications in the specifically described embodiments can be carried out without departing from the principles of the invention, which is intended to be limited only by the scope of the appended claims, as interpreted according to the principles of patent law including the doctrine of equivalents.

The invention claimed is:

1. A driver monitoring system for a vehicle, the driver monitoring system comprising:
   a camera disposed at an interior of the vehicle so as to view a face of a driver of the vehicle;
   wherein the camera captures image data and the captured image data includes image data representative of the face of the driver;
   an electronic control unit (ECU) comprising electronic circuitry and associated software, the electronic circuitry including an image processor that processes image data captured by the camera; and
   wherein the ECU, responsive to processing by the image processor of image data captured by the camera, (i) detects changes in reflections at the face of the driver and detects changes in skin color of the face of the driver and (ii) determines a heart rate of the driver based at least in part on the detected changes in the reflections at the face of the driver and the detected changes in skin color of the face of the driver.

2. The driver monitoring system of claim 1, comprising an illumination source disposed in the interior of the vehicle, wherein the illumination source, when electrically powered, emits non-visible light that illuminates at least a portion of the face of the driver of the vehicle.

3. The driver monitoring system of claim 2, wherein the illumination source emits near-infrared (NIR) light or infrared (IR) light.

4. The driver monitoring system of claim 1, wherein the ECU determines the heart rate at least in part responsive to determination, via processing by the image processor of image data captured by the camera, of movements of the face of the driver.

5. The driver monitoring system of claim 1, wherein the ECU, responsive to determining a change in heart rate greater than a threshold change over a predetermined period of time, generates an alert.

6. The driver monitoring system of claim 1, wherein the ECU, via processing by the image processor of image data captured by the camera to detect changes at the driver's eyes or to detect nodding of the driver's head, determines driver attentiveness.

7. The driver monitoring system of claim 6, wherein the ECU, responsive to determination that driver attentiveness is below a threshold level, generates an alert.

8. The driver monitoring system of claim 6, wherein the ECU, responsive to determination that driver attentiveness is below a threshold level, generates an output to a vehicle control system that controls at least one driving system of the vehicle to maneuver the vehicle.

9. A driver monitoring system for a vehicle, the driver monitoring system comprising:
   a camera disposed at an interior of the vehicle so as to view a face of a driver of the vehicle;
   wherein the camera captures image data and the captured image data includes image data representative of the face of the driver;
   an electronic control unit (ECU) comprising electronic circuitry and associated software, the electronic circuitry including an image processor that processes image data captured by the camera;
   wherein the ECU, responsive to processing by the image processor of image data captured by the camera, detects changes in reflections at the face of the driver;
   wherein the ECU determines a heart rate of the driver at least in part responsive to determination, via processing by the image processor of image data captured by the camera, of the changes in reflections at the face of the driver and changes in skin color of the face of the driver;

wherein the ECU, via processing by the image processor of image data captured by the camera to detect changes at the driver's eyes or to detect nodding of the driver's head, determines driver attentiveness; and wherein the ECU, responsive to determination that driver attentiveness is below a threshold level, generates an alert.

10. The driver monitoring system of claim 9, comprising an illumination source disposed in the interior of the vehicle, wherein the illumination source, when electrically powered, emits non-visible light that illuminates at least a portion of the face of the driver of the vehicle.

11. The driver monitoring system of claim 9, wherein the ECU determines the heart rate at least in part responsive to determination, via processing by the image processor of image data captured by the camera, of movements of the face of the driver.

12. A driver monitoring system for a vehicle, the driver monitoring system comprising:

a camera disposed at an interior of the vehicle so as to view a face of a driver of the vehicle;

an illumination source disposed in the interior of the vehicle, wherein the illumination source, when electrically powered, emits non-visible light that illuminates at least a portion of the face of the driver of the vehicle;

wherein, with the illumination source electrically powered, the camera captures image data and the captured image data includes image data representative of the face of the driver;

an electronic control unit (ECU) comprising electronic circuitry and associated software, the electronic circuitry including an image processor that processes image data captured by the camera;

wherein the ECU, responsive to processing by the image processor of image data captured by the camera, detects changes in reflections at the face of the driver;

wherein the ECU determines a heart rate of the driver at least in part responsive to determination, via processing by the image processor of image data captured by the camera, of the changes in the reflections at the face of the driver and changes in skin color of the face of the driver; and wherein the ECU, via processing by the image processor of image data captured by the camera to detect changes at the driver's eyes or to detect nodding of the driver's head, determines driver attentiveness.

13. The driver monitoring system of claim 12, wherein the illumination source emits near-infrared (NIR) light or infrared (IR) light.

* * * * *